United States Patent [19]

Strohmayer et al.

[11] Patent Number: 4,946,925

[45] Date of Patent: Aug. 7, 1990

[54] BRIDGE BIS(CYCLOHEXYLAMINE) CURING AGENTS FOR EPOXY RESINS

[75] Inventors: Herbert F. Strohmayer, Allentown; Jeremiah P. Casey, Emmaus; Peter A. Lucas, Allentown, all of Pa.

[73] Assignee: Air Products and Chemicals, Inc., Allentown, Pa.

[21] Appl. No.: 444,492

[22] Filed: Dec. 1, 1989

Related U.S. Application Data

[63] Continuation of Ser. No. 301,568, Jan. 25, 1989.

[51] Int. Cl.$^5$ .............................................. C08G 59/50
[52] U.S. Cl. .................................................... 528/122
[58] Field of Search ........................................ 528/122

[56] References Cited

U.S. PATENT DOCUMENTS

| | | | |
|---|---|---|---|
| 2,817,644 | 12/1957 | Stokal et al. | 260/47 |
| 3,321,438 | 5/1967 | Brooker et al. | 260/47 |
| 3,629,181 | 12/1971 | Basel et al. | 260/31.8 |
| 4,026,858 | 5/1977 | Andrews et al. | 528/122 X |
| 4,293,687 | 10/1981 | Weissel et al. | 528/346 |
| 4,417,010 | 11/1983 | Shimp | 523/466 |
| 4,447,586 | 5/1984 | Shimp | 525/504 |
| 4,554,342 | 11/1985 | Corley | 528/90 |
| 4,686,250 | 8/1987 | Qureshi | 52.3/440 |

FOREIGN PATENT DOCUMENTS

| | | |
|---|---|---|
| 907294 | 3/1954 | Fed. Rep. of Germany . |
| 3325895A1 | 1/1985 | Fed. Rep. of Germany ...... 564/457 |

*Primary Examiner*—Earl Nielsen

*Attorney, Agent, or Firm*—Russell L. Brewer; James C. Simmons; William F. Marsh

[57] ABSTRACT

This invention relates to bridged cyclohexylamines represented by the formula:

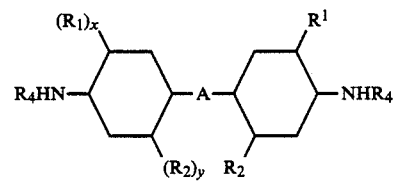

A is $C_0$, —$CH_2$—,

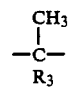

$R_1$ is $C_{1-3}$ alkyl
$R_2$ is $C_{1-6}$ alkyl
$R_3$ is $C_1$ or $C_2$ alkyl
$R_4$ is H or $C_{1-4}$ alkyl
x is 0 or 1
y is 0 or 1

These bridged bis(cyclohexylamine) derivatives are well suited as curing agents for epoxy resins. These compositions lead to enhanced processing of the epoxy resin and permit adjustment of the reactivity/performance in formulating epoxies which demonstrate superior high temperature properties.

22 Claims, No Drawings

BRIDGE BIS(CYCLOHEXYLAMINE) CURING AGENTS FOR EPOXY RESINS

This is a continuation of application Ser. No. 07/301,568, filed Jan. 25, 1989, pending.

TECHNICAL FIELD

This invention relates to bridged cyclohexylamine derivatives for use in preparing epoxies.

BACKGROUND OF THE INVENTION

Polyepoxide resins are widely known and have wide applications for use in automobile parts, springs, pipes and in the preparation of composite articles, as for example, by wet filament winding, compression molding, reaction injection molding and other techniques. They find such use because of their hardness, resistance to solvents and water, adhesion to metals and other surfaces, and other properties.

Conventionally, epoxy thermoset polymers are formed by reacting a glycidyl polyether of a polyhydric phenol with an amine, the amine acting as a curing agent for the epoxy resin. A wide variety of primary and secondary amine curing agents have been reported for use in curing epoxy resins in order to adjust the pot life of the epoxy resins for molding or winding, to impart long-term color stability and to impart resistance to sunlight and so forth. Primary amines are used to form crosslinked epoxy resins while secondary amines are used to formulate linear polyepoxide resins or used to react with polyfunctional epoxies to form crosslinked resins. Representative patents which show a variety of both aromatic and cycloaliphatic primary and secondary amines for use in preparing polyepoxide resins are as follows:

U.S. Pat. No. 3,321,438 discloses aliphatic and cycloaliphatic amines, including piperazines, as curing agents for fluidized bed polyepoxide coating compositions. Examples of alkyl-substituted diamines include: diethylene triamine, dimethyldaminodicyclohexylamine. propylenediamine and triethylene tetramine; cycloaliphatic diamines such as di(3-methyl-4-aminocyclohexyl)methane and di(4-aminocyclohexyl)methane and the N-substituted derivatives, e.g. N-cyclohexyl-1,3-propane diamine. Representative piperazines include aminobutylpiperazine and N-aminoisopropylpiperazine.

U.S. Pat. No. 2,817,644 discloses various curing agents for polyepoxides which comprise hydrogenated aromatic primary and/or secondary polyamines. Aromatic amines in their hydrogenated form include phenylenediamine, p,p'-methylenedianiline, 2,4-diaminotoluene, and N,N'-diphenylethylenediamine.

U.S. Pat. No. 3,629,181 discloses various cycloaliphatic and cycloaliphatic-aliphatic di-primary amines as a curing agent for polyepoxides. Representative di-primary amines include 1,4-diamino-3,6-diethylcyclohexane. 2,2-di(4-aminocyclohexyl)-propane, which is commonly referred to as hydrogenated bisaniline A, and 1-amino-3-aminomethyl-3,5,5-trimethyl-1-cyclohexane, which is commonly referred to as isophoronediamine.

U.S. Pat. No. 4,417,010 discloses a process for producing epoxy resins using liquid imidazole type curing agents. Many imidazole type curing agents were alleged as being difficult to use because they were solids or because they were too reactive resulting in premature gelation. Solvents were often used with the solid imidazole curing agents to enhance the effectiveness and this usually required higher temperatures and longer reaction times to drive off the solvent. By combining N,N'-dihydroxyethyl-5,5'-dimethyl hydantoin or trimethylpentanediol with a solid. eutectic forming imidazole, a liquid curing agent was obtained. Examples of imidazoles suited for use included 2-ethyl-4-methylimidazole and 2-phenylimidazole.

U.S. Pat. No. 4,447,586 discloses a process for producing polyepoxide resins using, in combination, a meta fluoborate (fluoroborate) and a hindered aromatic amine curing agent. Examples of liquid or low melting hindered aromatic amines include: diethyltoluenediamine, methylenebis(2,6-diisopropylaniline), methylenebis(2,6-diethylaniline) and methylenebis(2-methyl-6-ethylaniline).

U.S. Pat. No. 4,686,250 discloses a process for the preparation of moisture resistant wet winding epoxy resin systems using a polynuclear aromatic diamine or substituted derivative thereof as a curing agent. Examples of aromatic diamines include: 1,3-bis(4-aminophenoxybenzene), (TPE-R), and alpha,alpha'-bis(4-aminophenyl)-para-diisopropylbenzene.

SUMMARY OF THE INVENTION

This invention relates to bridged cyclohexylamines as curing agents for epoxy resins. The bridged cyclohexylamine curing agents are represented by the formula:

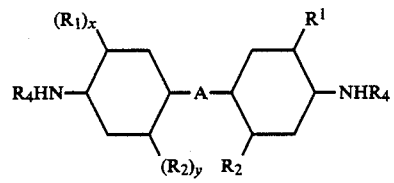

A is $C_0$, $-CH_2-$,

$R_1$ is $C_{1-3}$ alkyl
$R_2$ is $C_{1-6}$ alkyl
$R_3$ is $C_1$ or $C_2$ alkyl
$R_4$ is H or $C_{1-4}$ alkyl
x is 0 or 1
y is 0 or 1

The bridged cyclohexylamine derivatives when used as curing agents for epoxy resins provide many advantages over many prior art systems. Some representative advantages include:

an ability permitting formulators to adjust the reactivity of the system to optimize performance;

an ability to reduce reactivity by virtue of steric hindrance of the aliphatic substituent ortho to the amine coupled with the separate and isolated steric constraint supplied by the second aliphatic substituent;

an ability to adjust the molecular design of the diamine for specific applications in formulating epoxy resins having improved high temperature properties and longer pot life with low initial viscosity;

an ability to impregnate continuous knitted or woven fibers at room temperature;

operating flexibility in the plant through the use of liquid bridged cyclohexylamines which have lower vapor pressure than single ring diamines thus reducing handling problems: and an ability to produce stiff epoxy coatings with excellent flexural modulus and adhesion at elevated temperature.

DETAILED DESCRIPTION OF THE INVENTION

The polyepoxide resins which can be cured using the bis(cyclohexylamine) derivatives of this invention include those polyepoxides having more than on epoxy group per molecule with the epoxy group typically being a terminal 1,2-epoxy group. Although both liquid and solid epoxy resins can be used, polyepoxide resins which are liquid are preferred. These usually are based upon aromatic phenols and aliphatic polyols. Representative aromatic phenolic polyepoxides which can be used are glycidy polyethers of polyhydric phenols and are typically derived from a polyhydric phenol and an epichlorohydrin where the epoxide equivalent weight ranges from about 100 to 1000. Epichlorohydrins used for preparing the polyepoxide resin include epihalohydrins, such as epichlorohydrin and epibromohydrin. Polyhydric phenols are exemplified by resorcinol, hydroquinone, p,p'-dihydroxydiphenylmethane, p,p'-dihydroxydiphenylpropane or Bisphenol A, p,p'-dihydroxydiphenylethane and so forth. Of these polyepoxide resins, those based upon Bisphenol A are most common and preferred for the practice of this invention.

Other types of polyepoxide resins which can be cured with the biscyclohexyl derivatives are glycidyl polyester resins prepared by reacting an epihalohydrin with an aromatic or aliphatic polycarboxylic acid. Another type of polyepoxide resin is a glycidyl amine which is prepared by reacting a polyamine with an epichlorohydrin.

The bridged cyclohexylamines of this invention are suited for curing polyepoxide resins are represented by the formula:

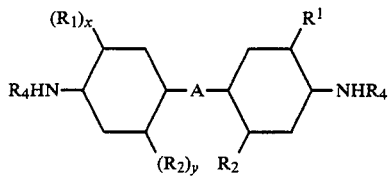

A is $C_0$, —$CH_2$—,

$R_1$ is $C_{1-3}$ alkyl
$R_2$ is $C_{1-6}$ alkyl
$R_3$ is $C_1$ or $C_2$ alkyl
$R_4$ is H or $C_{1-4}$ alkyl
x is 0 or 1
y is 0 or 1

The bridged cyclohexylamines represented by the above formula can be produced in accordance with general chemical procedures. One procedure involves the synthesis of a dialkyl-substituted aromatic hydrocarbon by reaction of benzene or toluene with an olefin to produce the para-substituted dialkyl aromatic hydrocarbon. This composition then is nitrated using conventional nitration techniques, e.g., the mixed nitric acid/sulfuric acid technique and then the resulting nitro group is reduced via hydrogenation using a hydrogenation catalyst. e.g., ruthenium or rhodium on alumina, palladium on carbon or palladium on alumina to form the amine derivative. The resulting amine derivative then is condensed with an aldehyde or ketone, e.g., formaldehyde acetone, acetophenone, fluorenone or methylethylketone to provide the preselected bridging group. The bridging group may be substituted with noninterfering substituents or unsubstituted as shown by the formulas and are deemed equivalent in such formulas. Once the bridged aromatic composition is formed, the aromatic rings can be reduced by conventional hydrogenation techniques. Hydrogenation is carried out under hydrogen pressure in the presence of a hydrogenation catalyst which is usually carried on a support such as silica or alumina.

In the curing of the polyepoxide resins using the bridged cyclohexylamine derivatives, it is preferred that one cyclohexyl ring as shown and the other cyclohexyl ring having at least one and preferably two alkyl substituents or radicals, i.e., both x and y are 1. When x and y are 0, then the ring has unsubstituted hydrogens for $R_1$. The steric hindrance provided by the alkyl groups ortho to the amine, i.e., in the 2,2'-position coupled with the steric hindrance by the alkyl groups in the 5 5'-position permits adjustment of the reactivity/performance characteristics. Because only one of the ortho positions to the amine is occupied, reactivity is not too slow for effective utilization as a curing agent and yet the blocking action of the alkyl groups in the 5,5'-position provides for reduced reactivity and 2,2'-substitution reduces conformational flexibility and thereby improves high temperature performance. Representative examples of diamines include:

2,2',5,5'-tetramethylmethylenedicyclohexylamine
2,2'-dimethyl-5,5'-diethylmethylenedicyclohexylamine
2,2',5,5'-tetraethylmethylenedicyclohexylamine
2,2'-dimethyl-5,5'-diisopropylmethylenedicyclohexylamine
2,2'-dimethyl-5,5'-tert-butylmethylenedicyclohexylamine
2,2',5,5'-tetramethyl-bis(4-aminocyclohexyl)propane
2,5'-dimethylmethylenedicyclohexylamine
2,2',5,5'-tetramethyldicyclohexylamine
2-methy,5-ethylbicyclohexylamine The polyepoxide resins are formed in conventional manner and can be reacted with the bridged cyclohexylamines under conventional conditions and preferably under conditions such that the rise in temperature of the reaction system is not more than about 10° C. The amount of bridged cycloaliphatic amine mixed with the polyepoxide resin should range from about 0.6 to 1.5 times the stoichiometric or equivalent amount of polyepoxide resin and preferably at a level from about 0.9 to 1.1 times the stoichiometric amount, stoichiometric being 2 equivalents epoxide per equivalent amine.

Conventional polyepoxide resins, plasticizers, fillers, pigments, solvents, etc. in formulating a coating for molding compositions can be used and the selection is at the option of the formulator. The adjustment of curing temperatures and curing times for polyepoxide resins, conventional accelerators can be incorporated as desired. Typically one is not required. However, representative accelerators include: boron trifluoride, amine complexes and metal fluoroborate systems, e.g., copper fluoroborate. Examples of polyepoxide resins, processing techniques, plasticizers, fillers, etc. for preparing epoxide resins are set forth in U.S. Pat. Nos. 4,685,250; 2,817,644 and 3,629,181 and are incorporated by reference.

The following examples are intended to illustrate various embodiment of the invention and are not intended to restrict the scope thereof.

EXAMPLE 1

TETRAMETHYLMETHYLENEDIANILINE PREPARATION

Tetramethylmethylenedianiline was prepared in the following manner. To a stirred 12 liter reaction flask was charged 2,5-dimethylaniline (762.3 gm or 6.3 moles), commercial paraxylidene) and deionized water (800 cc). The flask was immersed in a water bath at room temperature and a mixture of hydrochloric acid and water (620.8 g of 37% HCl, 6.3 moles, in 300 ml of deionized water) was added at a rate not exceeding 150 ml/min. Reactor temperature was allowed to gradually was increased to 35° C. through reaction. The reaction mixture was reddish and clear. Deionized water (800 cc) was added to the reddish and clear reaction mixture and the reactor chilled to 5° C. The cooled reaction mixture formed a precipitate in suspension.

Formaldehyde (255.4 g of 37% $CH_2O$ in water or 3.15 moles) was added at a rate not exceeding 30 ml/min to the reaction mixture for the formation of the methylene bridge. The temperature was held at around 6° C. during the addition. One liter of deionized water was added. The water bath was replaced by a heating mantle and gradual heating started. At 20° C. the reaction mixture was clear of precipitate and had a reddish color. The progress of the reaction was monitored by taking small samples (2-3 cc) from the reaction mixture, neutralizing and then analyzing by g.c. At 60° C. the reaction mixture suddenly solidified at which time approximately 6 l of deionized water was added. Stirring was restored and heating continued. A clear solution was obtained at approximately 90° C. After a clear solution was achieved, the reaction mixture showed essentially complete conversion of the starting material. To ensure the transformation of intermediates, the reaction was maintained at 90-95° C. for three hours. The intermediates content was not very high (ca. 1%) and the concentration of heavy by-products (trimer) remained essentially constant during the heating period. The heavy by-products were in the 5-7 wt % range. The product peak in the g.c. was in 93-95% range. At the end of the 3 hour heating period, the reaction mixture was transferred to a 5 gallon container by aspirator vacuum.

Upon cooling, a greenish-white precipitate was formed in the reaction mixture which could be brought into suspension by stirring. Extraction and neutralization of the product was carried out in a 4 l separatory funnel using several portions of the following composition for extraction:
150 cc 50% NaOH
375 cc tetrahydrofuran (THF)
1000 cc Product Mixture The combined extract from the three extractions was concentrated into a 5 l round bottom flask by distilling off THF at atmospheric pressure. As the solvent was removed, the contents of the distillation flask solidified. Water and the light ends, consisting mainly of the unreacted starting material paraxyidene, were removed by vacuum distillation (70 to 55 mm Hg with a 90 to 200° C. pot temperature). The distillation flask was allowed to cool under nitrogen and the bottoms in the pot solidified. A small nitrogen purge was maintained while the temperature of the pot was raised to 155° C. to melt the solids. Analysis of the melt by G.C. showed an absence of the paraxylidene starting material. The product was distilled at 0.45 mm Hg from 206° C. to 220° C. The high melting point (140° C.) of the product required the heating of transfer lines and the receiver to avoid line plugging, etc.

The heart-cut weighed 2001 g. The product had a very light yellow color. Purity of 2,2',5,5'-tetramethylmethylenedianiline (TMMDA) was 99.7%. A summary of the product distillation is reported below:

|  | Fore-cut (%) | Heart-Cut 2001 g (%) | Bottoms 364 g (%) | Total (%) |
| --- | --- | --- | --- | --- |
| paraxylidene | 0.5 | — | — | 0.5 |
| TMMDA | 0.3 | 83.6 | 0.5 | 84.4 |
| Trimmer | — | 0.2 | 14.7 | 14.9 |
| Total |  |  |  | 99.8 |

EXAMPLE 2

Hydrogenation of TMMDA to TMMDCHA using ruthenium catalyst

A portion of 2,2',5,5'-tetramethylmethylenedianiline (TMMDA), 254 g (1 mole) from Example 1 was slurried in 765 ml tetrahydrofuran and placed in a 2 liter autoclave. 10.2 g of 5% Ru on alumina catalyst obtained from the Englehard Corporation was added followed by 2.5 g anhydrous lithium hydroxide base promoter. The reactor was sealed and purged three times with nitrogen and then twice with hydrogen before being pressurized with hydrogen to 2100 psi. The reaction mixture was heated to 180° C. and maintained at 180° C. during the reduction. Stirring at a rate of 740 rpm was maintained during the reduction. The reactor pressure was allowed to drop to no lower than 1500 psi before being recharged to 2000 psi until slightly greater than stoichiometric hydrogen consumption had occurred (6.3 hours). At that time the reaction mixture was cooled, vented, and purged with nitrogen. The crude reaction solution was removed from the autoclave, filtered free of catalyst and analyzed by capillary chromatography. Product diamine isomers comprised 83.1% of the reaction crudes, with deaminate lights 4.1%, half-reduced TMMDA 9.0% and unreduced TMMDA 0.4%.

EXAMPLE 3

Hydrogenation of TMMDA using ruthenium - rhodium catalyst

In this example an alternative catalyst, in contrast to Example 2, was used for hydrogenation of TMMDA. More specifically 381.6 g (1.5 moles) of TMMDA was slurried in 500 ml tetrahydrofuran and placed in an autoclave. 21.3 g of a 5% Ru on alumina catalyst, 5.4 g of a 5% Rh on alumina catalyst and 2.7 g anhydrous LiOH base promote were added to the reactor. The reactor was purged thrice with nitrogen, thrice with hydrogen and then vented to atmospheric pressure before addition of 102 g of anhydrous ammonia. The reactor was pressurized with hydrogen to 3000 psi and the reaction mass brought to 180° C. Reactor pressure was maintained between 3000 and 2750 psig as hydrogen uptake rate was monitored. When slightly greater than stoichiometric hydrogen uptake was reached (5 hours), the reactor was cooled, vented and purged. The crude product analyzed or crude TMMDCHA 85%, lights 2.8%, half-reduced product (TMMDA) 11.9% and unreduced TMMDA 0.1%.

Isomer Distribution and Commentary Regarding TMMDCHA and Bridged Diamines

With two configurational centers in each ring the potential isomers in methylenedicyclohexylamine, (PACM, MDCHA) are (cis, cis), (cis, trans), (trans, cis) and (trans, trans). Due to the plane of symmetry in MDCHA the (cis, trans) and (trans, cis) isomers are equivalent, resulting in three isomers. In 3.3'-dimethylmethylenedicyclohexylamine (DMMDCHA) there are three chiral centers in each ring, and no plane of symmetry in the molecule. Within each ring the isomer combinations for the 1,2- and 4-position substituents are again four in number (c,c) (c,t) (t,c) and (t,t). Combining the rings leads to a factorial of 16 isomers possible in dimethylmethylenedicyclohexylamine (DMMDCHA). For TMMDCHA with four chiral centers in each ring and no plane of symmetry the possible configurational isomers are ccc, cct, ctc, ctt, tcc, tct, ttc and ttt in each ring for a factored total of 64 potential isomers. In the hydrogenations carried out in Example 2 and this Example 3 there are a dozen or so resolved peaks by capillary chromatography. Isomer distribution varies as a function of run conditions such as catalyst, temperature, and time. For Examples 2 and 3 the 8 major isomers, normalized to 100% TMMDCHA composition, vary as given below:

| Isomer peak | pk1 | pk2 | pk3 | pk4 | pk5 | pk6 | pk7 | pk8 |
|---|---|---|---|---|---|---|---|---|
| Ex. 2 | 9.8 | 9.5 | 25.9 | 27.9 | 3.2 | 3.6 | 10.0 | 10.0 |
| Ex. 3 | 5.4 | 6.0 | 33.2 | 37.9 | 8.4 | 7.7 | .8 | .6 |

EXAMPLE 4

Epoxy Resin Preparation and Testing

Three formulations were prepared to determine the reactivity profile of an epoxy resin against various diamines. The instrument used to measure reaction time in epoxy resin/amine curing formulations was a Sunshine ® Gel Time Meter. The principle of operation is based on a circuit disconnect once a glass rod reaches a specific torque. In testing, the rod is immersed in the resin/curing agent formulation which is held in a test tube, the test tube being suspended in a constant temperature bath. This torque is characteristic of a torsion spring of constant dimensions connected between the rod and the instrument.

A first formulation (1A) was prepared by mixing 100 parts by weight of the diglycidyl ether of Bisphenol A having an epoxide equivalent weight of 187 with 28.2 parts by weight of a commercial curing agent, sold under the trademark Amicure™ PACM (MDCHA) having an amine hydrogen equivalent weight (AHEW) of 52.5. The mixture was stirred at room temperature (22° C.) until homogeneous but no longer than five (5) minutes. Then 10 g of the mixture was placed in the test tube described above. The gel timer glass rod was placed into the mixture and the test tube secured in a waterbath preheated to 60° C. (140° F.). The glass rod was attached to the instrument and aligned so the rotating rod did not touch the sides of the test tube. The gel timer was turned on and allowed to run until a gel time was registered.

A second formulation (1B). was prepared and tested in a similar manner to formulation by 1A), substituting 32 parts by weight of 3,3'-dimethylmethylenedicyclohexylamine (DMMDCHA) (AHEW 59.5) for the amine Amicure PACM.

A third formulation (1C), was prepared and tested in a similar manner to Runs 1A and 1B using 35.6 parts by weight of 2,2',5,5'-tetramethylmethylenedicyclohexylamine (TMMDCHA) (AHEW 66.5) as the amine curing agent.

The results of the gel times are listed below:

| ISOTHERMAL GEL TIME @60° C. | | |
|---|---|---|
| Prior Art | Prior Art | TMMDCHA |
| Run 1A | Run 1B | Run 1C |
| PACM | 3,3' DMMDCHA | TMMDCHA |
| 23.2 min | 51.7 min | 73.0 min |

These results show a clear difference between the 2,2',5,5'-tetramethylmethylenedicyclohexylamine TMMDCHA and the commercial amine curing agent PACM in terms of gelation time, even though only one of the ortho to each amine group positions was blocked in TMMDCHA, as was the case with DMMDCHA.

EXAMPLE 5

Exotherm Profiles of Epoxy Resins

Exotherm profiles of the formulations of Example 4 were observed using a differential scanning calorimeter (DSC). Runs 2A, 2B, and 2C were identical in composition and in the mix procedure used to prepare runs 1A), 1B), and 1C) of Example 4. After each formulation was mixed, it was immediately weighed in a DSC sample pan on an analytical balance and placed in a DSC cell of a DuPont 9900 thermal analyzer. The cell was programmed to increase in temperature from 23° C. (73.4° F.) to 250° C. (482° F.) at a rate of 10° C./minute. Analysis of the resulting exotherms for each formulation indicated a shift in the location of the peak exotherm for the slower reactivity formulations.

| DSC REACTIVITY PROFILE | | | |
|---|---|---|---|
| | PACM | DMMDCHA | TMMDCHA |
| | Run 2A | Run 2B | Run 2C |
| Onset Temperature, °C. | 88 | 91 | 96 |
| Peak Temperature, °C. | 113 | 124 | 128 |
| ΔH, Joules/g | 413 | 304 | 325 |

EXAMPLE 6

Epoxy Resin Testing

In order to demonstrate the development of cure properties, samples 3A), 3B), and 3C) were prepared. The formulation compositions and mix procedure were identical to those used to prepare runs 1A), 1B), and 1C) of Example 4. Each sample was degassed and then poured into a ⅛" thick casting. A separate casting was made for each cure schedule. Glass transition temperatures were run on the cured castings to determine the extent of cure. This was accomplished through the use of a differential scanning calorimeter (DSC) which was programmed with a 10° C./minute rate of increase from 23° C. to 280° C. Upon completion of the scan, each sample was cooled to 23° C. in the DSC cell using a dry ice cold finger and a second scan was run under identical conditions. Table 1 reports results for both scans noting residual exotherms where no glass transition occurred.

TABLE 1

CURE AND GLASS TRANSITION TEMPERATURE °C.

| | | | \multicolumn{7}{c}{CURE SCHEDULE HRS/°C.} |
|---|---|---|---|---|---|---|---|---|---|
| RUN | SCAN | SAMPLE | 1/80 | 2/80 | 2/80 1/150 | 2/80 2/150 | 2/80 3/150 | 2/80 2/80 1/200 | 2/80 3/150 2/200 |
| 3A | First | PACM | Exo | Exo | 147 | 147 | 152 | 156 | 154 |
| | Second | | 160 | 160 | 158 | 159 | 159 | 155 | 156 |
| 3B | First | DMMDCHA | Exo | Exo | 115 | 127 | 133 | 147 | 148 |
| | Second | | 138 | 146 | 146 | 145 | 148 | 152 | 154 |
| 3C | First | TMMDCHA | Exo | Exo | 163 | 170 | 167 | 176 | 187 |
| | Second | | 182 | 186 | 184 | 180 | 185 | 186 | 188 |

The above results show markedly superior thermal performance of TMMDCHA and rapid development of the thermal properties relative to the conventional and commercial cycloaliphatic diamines, i.e., PACM and DMMDCHA. The higher glass transition temperature of the epoxy resin cured with TMMDCHA also provides for finished thermoset with a useful life over a wide temperature range.

EXAMPLE 7

Mechanical Property Performance of Epoxy Resin Formulations

In order to demonstrate mechanical property performance imparted by the amine compositions, samples 4A), 4B), and 4C) were prepared. Their composition and mix procedure were identical to those of runs 1A, 1B, and 1C of Example 4.

Each sample was degassed prior to pouring into ⅛" thick castings. The castings were gelled and post cured. Mechanical properties were examined using coupons from these castings in accordance ASTM standards. Tests were carried out at 23° C. The cure schedule and tests results are reported in Table 2.

TABLE 2

PHYSICAL PROPERTIES

| RUN | 4A PACM | 4B DMMDCHA | 4C TMMDCHA |
|---|---|---|---|
| Cure Schedule | 2 Hrs @ 80° C. +2 Hrs @ 150° C. +2 Hrs @ 200° C. | 2 Hrs @ 80° C. +2 Hrs @ 150° C. +2 Hrs @ 200° C. | 2 Hrs @ 80° C. +3 Hrs @ 150° C. |
| Flexural Strength, psi | 23,900 | 21,400 | 23,700 |
| Flexural Modulus, psi × $10^5$ | 5.11 | 5.15 | 4.84 |
| Tensile Strength, psi | 10,400 | 10,100 | 9,500 |
| Tensile Modulus, psi × $10^5$ | 3.25 | 3.53 | 5.09 |
| Elongation, % | 5.47 | 3.80 | 3.88 |

The above results show superior tensile modulus was obtained with the epoxide resin cured with TMMDCHA. It exhibited superior tensile modulus relative to the commercial aromatic amines without sacrificing other physical properties.

COMPARISON EXAMPLE 8

Tetraalkylmethylenedicyclohexylamine

As a counter example of a tetra-alkyl substituted methylenedicyclohexylamine, i.e., 3,3'-dimethyl-5,5'-diethylmethylenedicyclohexylamine where both ortho positions to the amine were blocked with methyl and ethyl groups was used as the amine curing agent. A formulation was prepared as in Example 7 using 39.3 parts by weight of this diamine (AHEW 73.5). The gel time at 60° C. was 190.3 min in contrast to the 73 minutes obtained with 2,2',5,5'-tetramethylenedicyclohexylamine.

A casting was also made as using the following cure schedule: 2 hr @ 80° C., 2 hr @ 150° C. and then 2 hr @ 100° C. The glass transition temperature using the DSC procedure previously cited was only 125° C. Flexural strength and modulus tested at 23° C. were 22,700 psi and 6.04×$10^5$ psi, respectively, while the drop in mechanical performance derived from the E' values of the DMA was observed at 116.9° C.

From the above data the delayed reactivity of the 3,3',5,5'-tetraalkylmethylenedicyclohexylamine as a curing agent is manifest vis-a-vis PACM, DMMDCHA and even TMMDCHA. Although extended delayed reactivity may be an advantage in some instances, the advantages associated with the delayed activity of the tetraalkylmethylenedicyclohexylamine are reduced by virtue of the poor glass transition temperature of the resulting epoxy resin. To summarize, the tetra-alkyl substitution pattern, i.e. the 2,2',5,5'- pattern of the claimed diamines has a significant effect on the physical properties of the resulting epoxy resin, first by retarding activity of the amine as a curative and second by enhancing thermal properties from retarded notation around the ring of the diamine by virtue of the alkyl groups in the 2 and 2'-position.

What is claimed is:

1. A polyepoxide resin comprising the reaction product of a glycidyl polyether of a polyhydric phenol having terminal 1,2- epoxy groups cured with a bridged dicyclohexylamine represented by the formula:

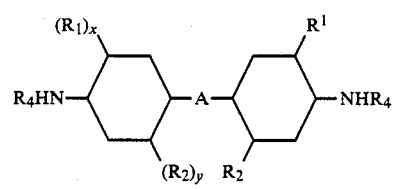

wherein

A is —CH$_2$—,

R$_1$ is C$_{1-3}$ alkyl
R$_2$ is C$_{1-6}$ alkyl
R$_3$ is C$_1$ or C$_2$ alkyl
R$_4$ is H or C$_{1-4}$ alkyl
x is 0 or 1 and
y is 0 or 1

2. The polyepoxide resin of claim 1 wherein x and y are 1.

3. The polyepoxide resin of claim 2 wherein A is —CH$_2$—.

4. The polyepoxide resin of claim 3 wherein R$_4$ is hydrogen.

5. The polyepoxide resin of claim 4 glycidyl polyether of a polyhydric phenol is the reaction product of Bisphenol A and epichlorohydrin.

6. The polyepoxide resin of claim 5 wherein the bridged cyclohexylamine is reacted with the glyidylpolyether of a polyhydric phenol in a proportion of 0.9 to 1.1 equivalents amine per equivalent terminal epoxy group.

7. The polyepoxide resin of claim 6 wherein R$_1$ is methyl.

8. The polyepoxide resin of claim 7 wherein R$_2$ is methyl.

9. The polyepoxide resin of claim 7 wherein R$_2$ is ethyl.

10. The polyepoxide resin of claim 7 wherein one R$_2$ is methyl and the other R$_2$ is ethyl.

11. The polyepoxide resin of claim 7 wherein R$_2$ is isopropyl.

12. The polyepoxide resin of claim 7 wherein R$_2$ is tert-butyl.

13. The polyepoxide resin of claim 2 wherein A is

14. The polyepoxide resin of claim 13 wherein R$_3$ is CH$_3$.

15. The polyepoxide resin of claim 14 wherein R$_4$ is hydrogen.

16. The polyepoxide resin of claim 15 wherein R$_1$ is methyl.

17. The polyepoxide resin of claim 16 wherein R$_2$ is methyl.

18. The polyepoxide resin of claim 16 wherein R$_2$ is ethyl.

19. The polyepopide resin of claim 16 wherein one R$_2$ is methyl and the other R$_2$ is ethyl.

20. The polyepoxide resin of claim 16 wherein R$_2$ is isopropyl.

21. The polyepoxide resin of claim 16 wherein R$_2$ is tert-butyl.

22. The polyepoxide resin of claim 16 wherein one R$_2$ is methyl and the other is tert-butyl.

* * * * *